United States Patent
Gokhale et al.

(10) Patent No.: US 11,270,791 B2
(45) Date of Patent: Mar. 8, 2022

(54) IN SILICO METHODS FOR OBTAINING NUTRACEUTICAL COMPOSITIONS

(71) Applicant: TATA CHEMICALS LIMITED, Mumbai (IN)

(72) Inventors: Sucheta Gokhale, Pune (IN); Anirban Bhaduri, Pune (IN)

(73) Assignee: TATA CHEMICALS LIMITED, Mumbai (IN)

( * ) Notice: Subject to any disclaimer, the term of this patent is extended or adjusted under 35 U.S.C. 154(b) by 6 days.

(21) Appl. No.: 16/833,274

(22) Filed: Mar. 27, 2020

(65) Prior Publication Data
US 2020/0312438 A1    Oct. 1, 2020

(30) Foreign Application Priority Data
Mar. 30, 2019 (IN) .............................. 201921012945

(51) Int. Cl.
| | |
|---|---|
| G16H 20/90 | (2018.01) |
| G16B 5/00 | (2019.01) |
| G16H 10/40 | (2018.01) |
| G16H 15/00 | (2018.01) |
| G16H 50/70 | (2018.01) |
| G16H 50/20 | (2018.01) |
| G16H 70/60 | (2018.01) |

(52) U.S. Cl.
CPC .............. *G16H 20/90* (2018.01); *G16B 5/00* (2019.02); *G16H 10/40* (2018.01); *G16H 15/00* (2018.01); *G16H 50/20* (2018.01); *G16H 50/70* (2018.01); *G16H 70/60* (2018.01)

(58) Field of Classification Search
USPC .......................................... 705/2–3; 977/896
See application file for complete search history.

(56) References Cited

U.S. PATENT DOCUMENTS

| | | | | |
|---|---|---|---|---|
| 2009/0182579 | A1* | 7/2009 | Liu ........................ | G16H 50/20 705/3 |
| 2009/0259489 | A1* | 10/2009 | Kimura .................. | G16B 50/20 705/3 |
| 2012/0196321 | A1* | 8/2012 | Famili .................. | C12N 9/0071 435/41 |
| 2016/0030494 | A1* | 2/2016 | Henn .................... | A61K 35/741 424/282.1 |
| 2016/0206666 | A1* | 7/2016 | Falb ........................ | A61K 38/26 |

FOREIGN PATENT DOCUMENTS

WO        2018/187272        10/2018

OTHER PUBLICATIONS

Rizk et al., "An Ensemble Modeling Framework for the Simulation and Optimization of Metabolic Networks", University of California, Los Angeles, 2009, pp. 1-111, (Year: 2009).*
Thiele and Palsson; *A protocol for generating a high-quality genome-scale metabolic reconstruction*; Jan. 7, 2010.

(Continued)

*Primary Examiner* — Amber A Misiaszek
(74) *Attorney, Agent, or Firm* — Workman Nydegger

(57) ABSTRACT

The present disclosure relates to methods and systems for obtaining a nutraceutical composition. The method comprises the use of genome-scale metabolic networks of microorganisms to identify nutraceutical compositions for one or more health conditions.

15 Claims, 9 Drawing Sheets

(56) References Cited

OTHER PUBLICATIONS

Raman and Chandra; *Flux balance analysis of biological systems: applications and challenges*; Briefings in Bioinformatics. vol 10. No. 4. 435-449; Mar. 15, 2009.
Sivakumar et al.; *ReactPRED: a tool to predict and analyze biochemical reactions*; Bioinformatics, 32(22), 2016, 3522-3524 doi: 10.1093/bioinformatics/btw491; Aug. 2, 2016.

* cited by examiner

IN SILICO METHODS FOR OBTAINING NUTRACEUTICAL COMPOSITIONS

FIELD OF INVENTION

The present disclosure relates to the field of computer-implemented methods for the design of compositions. There is provided an in silico method for obtaining nutraceutical compositions.

BACKGROUND

The human gut microbiome comprises a heterogenous collection of microorganisms, predominantly bacteria, that contribute to the host metabolism in several ways. Interactions between gut microbiota and the host have significant roles in conferring host protection against invading pathogen, regulation of diverse host physiological functions including metabolism, development and homeostasis of immunity and the nervous system. Changes within the gut microbiota are now understood to contribute to the development of several diseases including, for example, metabolic disorders such as diabetes and obesity, immunological disorders, cancer, and allergies among others.

These microorganisms live symbiotically within the human gut. Essentially, the microbiome is able to metabolise many of the metabolites and molecules produced by the human body and utilise them for the microorganisms' physiological functions. Alternatively, these microorganisms are also able to produce several metabolites that have therapeutic function within the human body and therefore contribute to the overall health and well-being of the individual.

Owing to the diversity in the composition of the human microbiome and the complexity in the metabolic interactions between metabolites and microorganisms, coupled with the interactions between the microorganisms themselves, studies have now utilized large scale genome sequencing projects to sequence the human microbiota and apply metabolomics to attribute genome level information into the network of metabolic pathways functioning with the microorganisms. This has been successful in providing a route to examine the potential impacts of diet, antibiotics, and environmental toxicants, on the microbiota and disease manifestation, due to changes in microbiota composition, transcriptomes, proteomes or metabolomes. The information retrieved from such studies is then used to optimize disease treatment and dosage requirements of different nutraceuticals.

Such studies, however, primarily rely on in vivo experimentation to optimize and validate the dosage requirements of different metabolites and nutraceuticals to accurately predict the effect of such treatments on specific health conditions. Such experiments are time consuming and subject to human error. Further, although in silico models exist (Magnúsdóttir, Stefanía, et al., *Nature biotechnology* 2017, 35.1, 81), these may not predict the effects of different metabolites and nutraceuticals due to their limited functional capability owing to their incompleteness.

There is therefore a need to accurately determine the effects of different compositions on the gut microbiota to alleviate disease symptoms and promote health and wellness.

SUMMARY

In an aspect of the present disclosure, there is provided a method for obtaining a nutraceutical composition, the method comprising: receiving, by a control unit, at least one user input selected from the group consisting of a microorganism, a nutraceutical, a health condition and combinations thereof; extracting, by the control unit, from a database having information related to a plurality of microorganisms, nutraceuticals and health conditions, and one or more sets of reaction rules derived from the enzymes reported within the plurality of microorganisms, at least one genome-scale metabolic network corresponding to the user input, wherein the metabolic network is based on the one or more sets of reaction rules; and generating, by the control unit, the nutraceutical composition based on the extracted at least one genome-scale metabolic network.

In another aspect, there is provided a system for obtaining a nutraceutical composition comprising: a display unit; at least one database having information related to a plurality of microorganisms, nutraceuticals and health conditions, and one or more sets of reaction rules derived from the enzymes reported within the plurality of microorganisms; a control unit (100) operatively coupled to the display unit, and the at least one database, the control unit (100) being configured to: receive at least one user input via the display unit, the user input being selected from the group consisting of a microorganism, a nutraceutical, a health condition and combinations thereof; extract, from the database, at least one genome-scale metabolic network based on the user input; and generate at least one nutraceutical composition based on the received at least one user input and the extracted at least one genome-scale metabolic network.

In a further aspect of the present disclosure, there is provided a method for obtaining at least one nutraceutical composition for a plurality of health conditions comprising: receiving, by a control unit, at least one user input including a microorganism, and a nutraceutical; extracting, by the control unit, at least one genome-scale metabolic network corresponding to the user input, from a database having information related to a plurality of microorganisms, nutraceuticals and health conditions, and one or more sets of reaction rules obtained from enzymes of the plurality of microorganisms, wherein the metabolic network is based on the one or more sets of reaction rules; and generating, by the control unit, from the genome-scale metabolic network and the nutraceutical of user input, the at least one nutraceutical composition for the plurality of health conditions.

In another aspect of the present disclosure, there is provided a method for obtaining a plurality of nutraceuticals for a health condition comprising: receiving, by a control unit, at least one user input including a microorganism, and a health condition; extracting, by the control unit, at least one genome-scale metabolic network corresponding to the user input, from a database having information related to a plurality of microorganisms, nutraceuticals and health conditions, and one or more sets of reaction rules obtained from enzymes of the plurality of microorganisms, wherein the metabolic network is based on the one or more sets of reaction rules; and generating, by the control unit, from the genome-scale metabolic network and the health condition of the user input, the plurality of nutraceuticals for a health condition.

DETAILED DESCRIPTION

Figure 1:
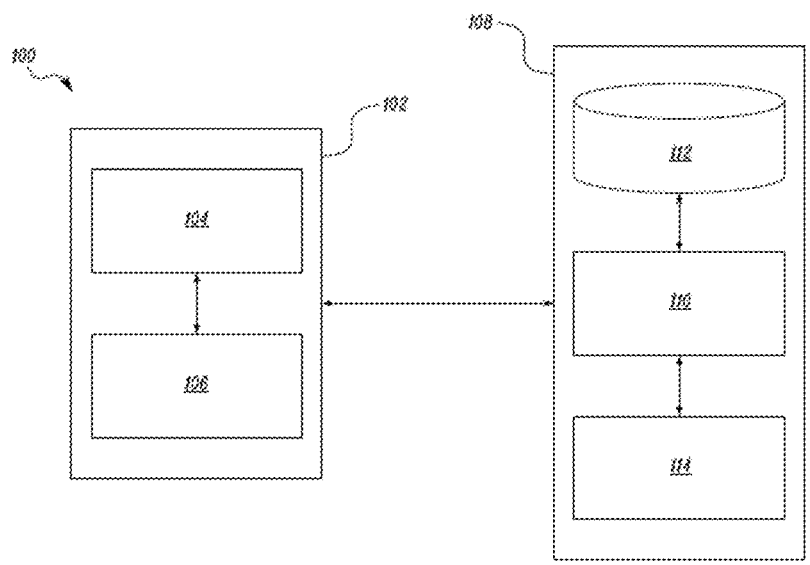
FIG. 1 illustrates a block diagram of an exemplary data processing system 100 for processing data relating to obtaining one or more nutraceutical compositions.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are explanatory of the invention and are not intended to be restrictive thereof.

The terms "a," "an,", and "the" are used to refer to "one or more" (i.e. to at least one) of the grammatical object of the article.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion and are not intended to be construed as "consists of only", such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Likewise, the terms "having" and "including" and their grammatical variants are intended to be non-limiting, such that recitations of said items in a list is not to the exclusion of other items that can be substituted or added to the listed items.

The term "nutraceutical" refers to products and compounds that provide health benefits to a host organism. These products and compounds may include vitamins, minerals, herbs and other botanicals, amino acids, carbohydrates, and metabolites and compounds that are metabolizable by microorganisms in a host organism. A nutraceutical may be obtained from natural plant or animal-based sources or may be synthesized molecules.

The term flux, or metabolic flux is the rate of turnover of molecules through a metabolic pathway. Flux is regulated by the enzymes involved in a pathway. The regulation of flux is vital for all metabolic pathways to regulate the pathway's activity under different conditions.

The term "organism" when used herein in reference to the genome annotated metabolic models, metabolic networks and metabolic processes, refer to microorganisms including bacteria and yeasts among others.

The terms "microorganism" and "microbe" are used interchangeably throughout the specification and claims.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure relates to a system for obtaining a nutraceutical composition. FIG. 1 illustrates a block diagram of an exemplary data processing system 100 for processing data relating to obtaining one or more nutraceutical compositions. The data processing system 100 depicted in FIG. 1 may be implemented in any suitable computing environment, such as, a desktop or laptop computer, a computer server, or a mobile computing device, such as a mobile phone, a Personal Digital Assistant (PDA), or a smart phone. In addition, the data processing system 100 may be combined into fewer systems than shown, or divided into more systems than shown. The communications links depicted in FIG. 1 may be through wired or wireless connections and may be part of a secured network, such as a local area network (LAN) and/or a combination of networks, such as LANs, WANs, MANs and/or the Internet.

According to an embodiment of the present disclosure, the data processing system 100 includes an Input/Output unit 102, hereinafter referred to as I/O unit 102. The I/O unit includes an output unit 104 and an input unit 106. The output unit 104 may include a display unit having a screen such as one or more of a computer screen, a mobile screen, or a television screen. The output unit 104 serves as a means for a user to visualize data that has may be entered by the user using the input unit 106, and to optionally visualize data that may be generated by a control unit 108.

The input unit 106 serves as means for the user to input values and provide instructions to the control unit 108 for processing data associated with the inputted values. The input unit 106 also serves as means for the user to manipulate, study, and the screen data, received from the control unit 108. In one embodiment, the input unit 106 may include a keyboard and/or a mouse, a joystick. Alternatively, or in combination with the keyboard and/or the mouse, the input unit 106 may also be a hands free voice-controlled device. In another embodiment, the input unit 106 and the output unit 104 may be part of the same device, and may take the form of a device, such as a tablet, a mobile, or touchscreen computer. The I/O unit may be operatively linked to the control unit 108.

The control unit 108 includes a processing unit 110. The processing unit 110 may include microprocessors, microcomputers, microcontrollers, digital signal processors, central processing units, state machines, logic circuitries, and/or other devices. The control unit 108 also includes a communication unit 114. The communication unit 114 may include a modem, an Ethernet card, or other similar devices, which enable the control unit 108 to connect to databases and networks. The control unit 108 facilitates input from a user through the Input/Output unit 102.

Among other capabilities, the processing unit 110 may fetch and execute programmable or computer-readable instructions. One or more programmable or computer-readable instructions may include various commands that instruct the control unit 108 to perform specific tasks, such as steps that constitute the method of the disclosure. The processing unit 110 described may also be implemented using only software programming or using only hardware or by a varying combination of the two. The computer-readable instructions may be written in programming languages including, but not limited to, 'C', 'C++', 'Visual C++' and 'Visual Basic'. Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. Aspects of the disclosure can be implemented in various operating systems and platforms including, but not limited to, 'Unix', 'DOS', 'Android', 'Symbian', and 'Linux'.

The computer-readable instructions can be stored and transmitted via a computer-readable medium. The disclosure can also be embodied in a computer program product including a computer-readable medium, or with any product capable of implementing the above methods and systems, or the numerous possible variations thereof.

Among other capabilities, the processing unit 110 may fetch and execute computer-readable instructions stored in a database 112 coupled to the processing unit 110. The database 112 can be internal or external to the control unit 108 and maybe accessed through cloud computing. The database 112 may include any non-transitory computer-readable storage medium including, for example, volatile memory (e.g., RAM), or non-volatile memory comprising a storage device such as a hard disk drive, or a removable storage drive, such as, a floppy-disk drive, optical-disk drive, and the like. The storage device may also be a means for loading computer programs or other instructions into the computer system.

The database 112 includes information regarding a plurality of microorganisms, nutraceuticals, and health conditions.

The information regarding the microorganisms comprises a plurality of genome annotated metabolic models corresponding to the plurality of microorganisms in the database. The genome annotated metabolic models refer to mathematical reconstructions of all the known metabolic reactions occurring within an organism. This information of the complete set of metabolic reactions is correlated to the sequences of those genes and proteins known to have functions in the metabolic reactions of the organism. The reconstructions, therefore, collect all the information regarding the metabolic processes within the microorganism, and represent it in the form of a mathematical model. In a preferred embodiment, the microorganisms selected for the database include microorganisms residing in the gut of an organism, specifically the human gut microbiota. The metabolic models are stored in the database in the form of a metabolite-reaction matrix representing all the metabolites that are processed or exchanged in by each of the plurality of the microorganisms in the database and the reactions occurring within the organism. In an example implementation, every row of the matrix represents one unique metabolite and every column represents one reaction. The entries in each column are the stochiometric coefficients of the metabolites participating in the reaction. In this manner, the metabolite-reaction matrix specifies the reaction constraints for each metabolite represented in a genome annotated metabolic model of a microorganism.

One or more of such metabolite-reaction matrices for the each of the plurality of microoganisms may be obtained from publicly available databases and literature. Examples of such sources include BiGG Models, BioCyc, MetaNetX.org, Biomodels database, VMH database, Machado, Daniel, et al., *Nucleic acids research* 2018, 46.15, 7542-7553. The user may also periodically update the metabolite-reaction matrices with further data as and when new and more accurate data is obtained. These data may comprise experimental data obtained through privileged and/or personal communications, published experimental data, or updates to the data sets available from publicly available databases. Updates on the preliminary genomic models may be done manually by the user or through an automated program that periodically accesses selected databases to download recent updates to genomic models or their associated metabolic reaction pathways.

In one aspect, a genome-annotates metabolic model may not be available for specific microorganisms. In such a case, a preliminary metabolite-reaction matrix is built by deriving information regarding the genomic information and the known metabolic reactions and enzymatic pathways within such microorganisms. For instance, data for the annotated genome sequences of microbes can be obtained through publicly available databases comprising, for instance, The European Nucleotide Archive (ENA), Ensembl Bacteria, Genomes Online Database (GOLD), Integrated Microbial Genomes & Microbiomes(IMG/M), Uniprot, and combinations thereof. Data regarding metabolites and enzymatic pathways functioning with the microorganisms can be obtained through publicly available databases comprising sources, such as, Chemical Entities of Biological Interest (ChEBI), Kyoto Encyclopedia of Genes and Genomes (KEGG), METLIN, Pubchem, KNApSAcK, BRENDA, KO (KEGG Orthology) database. Microorganism and metabolic data from sources as described above may be integrated into a metabolite-reaction matrix using approaches such as MG-RAST, RAST, SEED and similar such applications.

In a further embodiment, the database 112 also comprises a plurality of genome scale metabolic networks of one or more of the plurality of microorganisms. These genome scale metabolic networks are built by the control unit 108 by integrating a plurality of genome annotated metabolic models associated with one of the plurality of microorganisms. Once the control unit 108 builds a genome scale metabolic network for one or more of the microorganisms, the control unit 108 stores the genome scale metabolic network in the database 112, for future use.

In an example implementation, the microorganisms in the data include species that are present within the gut of an organism. Preferentially, the organism is a mammal and more preferably a human. Examples of microbes present within the human gut can be selected from a group consisting of species from genera *Lactobacillus, Feacalibacterium, Bifidobacterium, Ruminococcus, Coprococcus, Dorea, Lachnospira, Roseburia, Butyrivibrio, Clostridium, Megamonas, Acidaminococcus, Succinispira, Megasphaera, Lactonifactor, Dialister, Pelosiunus, Veillonella, Acidamonas, Megamonas, Akkermansia*, and combinations thereof. The list of microorganisms described above is not meant to be exhaustive and may include any other microorganism species which are found or maybe discovered subsequently within the human gut. This list also includes species which may only occur during certain disease conditions of an individual which are otherwise not present or under-represented in the gut microbiota under normal circumstances.

In an embodiment of the present disclosure, the database 112 comprises information regarding nutraceuticals. The nutraceuticals described herein are associated with the metabolic pathways of the microorganisms in the database, such that these nutraceuticals are readily metabolised by the enzymes and enzymatic reactions occurring within these microorganisms. The maximum and minimum flux values of each nutraceutical is included in the database and correlated with the metabolic pathways in which each of the plurality of nutraceuticals may be assimilated in. In this manner, the reaction constraints for each of the metabolic pathways and the associated nutraceutical(s), are stored within the database, thus providing estimates for the metabolism of such molecules within the gut of an organism. Data pertaining to the flux values and additional data such as recommended dietary allowances (RDA) can be obtained through experimental values obtained through experimentation and/or published literature and databases such as FooDB, United States Envrionmental Protection Agency—Chemistry Dashboard, Chemical Entities of Biological Interest (ChEBI), Kyoto Encyclopedia of Genes and Genomes (KEGG), METLIN, Pubchem, KNApSAcK, BRENDA, KO (KEGG Orthology) database.

In another embodiment of the present disclosure, the database 112 also comprises a plurality of metabolic markers of health conditions. Markers included in the database include molecules and compounds comprising short chain fatty acids such as butyrates, propionate, lipids, carbohydrates, bile salts, siderophores, insulin, and combinations thereof. These molecules are well known indicators of specific health conditions. Examples of such health conditions include metabolic disorders comprising obesity, Cardiovascular Disease, and Type I and Type II diabetes, immunological disorders such as inflammatory bowel diseases, Crohn's disease, and irritable bowel syndrome, food allergies, asthma, acute infections, neurological disorders comprising depression, and anxiety, among others. Microorganisms in the gut of an organism are known to influence the levels of these metabolic markers through the metabolic reaction pathways. They are capable of metabolising or releasing these molecules and therefore change the levels of these markers correspondingly within an organism's body. Additionally, factors such as the presence of a disease, food intake habits, consumption of antibiotics, and other such factors are known to affect the microbial physiological activity within the gut, thereby exacerbating or resulting in various health conditions such as those listed herein. The same markers can be used to assess whether chosen composition parameters are likely in aiding in alleviating certain health conditions. Additionally, these markers can also be used to assess whether chosen composition parameters are able to promote the long term health and wellness of an organism. In an example implementation, for instance, suitable composition parameters comprising one or more nutraceuticals and one or more microorganisms can be chosen to increase the levels of certain vitamins within the body. Such a composition can be taken as a dietary supplement and can be used as a substitute for synthetic dietary supplements, thereby promoting the overall health and wellness of an individual.

According to an implementation of the present disclosure, the database 112 comprises a plurality of sets of reaction rules. The reaction rules also include reaction steps and reaction constraints of reacting molecules, wherein the reaction rules can be extrapolated to similar molecular species for predicting similar reaction pathways. The reaction rules used in the present disclosure include, for instance, C(C(=O)[O—])O—>C(=O)C(=O)[O—]+H. The reaction rules, as described herein, comprise reactions associated with the metabolic pathways of each of the plurality of the microorganisms in the database. More specifically, the reaction rules are derived from enzymes within the microorganisms. In one embodiment, a single set of reaction rules may be associated with only a specific microorganism. In another embodiment, one or more of the same sets of reaction rules maybe applicable to multiple microorganisms within the database 112. Reaction rules include biochemical reaction transformation rules and general chemical rules that are well understood and familiar to a person skilled in the art. In general, these reaction rules relate to the mechanism of action, and the criteria relevant for the progress of different biochemical reactions occurring in the metabolic pathways of one or more microorganisms. These mechanisms of action can then be extrapolated to similar metabolites involved in these biochemical reactions, thereby allowing for the prediction of the progression and outcome of the biochemical reaction. The reaction rules can therefore be used for two-way prediction of reactions in silico, i.e. both forward and retrosynthetic reactions can be predicted accurately. The reaction rules are added to the database and are based on experimental data and publicly available literature. An exemplary approach to biochemical pathway prediction using reaction rules is described in Sivakumar et al., 2016; *Bioinformatics*, 32, 3522-3524.

In an embodiment of the present disclosure, the database 112 maybe a single database or may comprise multiple databases that may be located in different locations. The multiple databases may store all of the components of the information described above, or may comprise parts of the information described above. For instance, a first database may store the information related to the microorganisms, a second database may store information related to the nutraceuticals, and a third database may store information related to the metabolic markers.

It may be contemplated that the databases described herein may include data repositories, or other data sources. In some embodiments, the databases may be implemented using a relational database, such as Sybase, Oracle, CodeBase and Microsoft® SQL Server as well as other types of databases such as, for example, a flat file database, an entity-relationship database, and object-oriented database, a record-based database, or the like.

Those skilled in the art will appreciate that any of the aforementioned steps and/or system modules may be suitably replaced, reordered, or removed, and additional steps and/or system modules may be inserted, depending on the needs of a particular application, but without departing from the scope and spirit of the disclosure. In addition, the systems of the aforementioned embodiments may be implemented using a wide variety of processes and system modules not discussed herein, and is thus not limited to any particular computer hardware, software, middleware, firmware, microcode, or the like.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

INDUSTRIAL APPLICABILITY

The present disclosure relates to an in silico method of obtaining one or more nutraceutical compositions. The method utilizes a constraints-based methodology to accurately determine the effects of a composition in alleviating disease symptoms and promoting health and wellness. The compositions preferably comprise one or more nutraceuticals and one or more microorganisms that maybe present within the human gut or maybe added as a probiotic. Such a composition is able to affect the physiological activity of one or more of the microorganisms in the human gut which are then able to affect metabolic changes within the host and consequently promote the health and wellness of the host. Unique to this method is the application of one or more reaction rules associated with enzymes within the microorganisms. These reaction rules enable the accurate prediction of metabolic reactions within a microorganism and therefore, help to accurately determine the effect of the compositions within the host gut.

Figure 2:
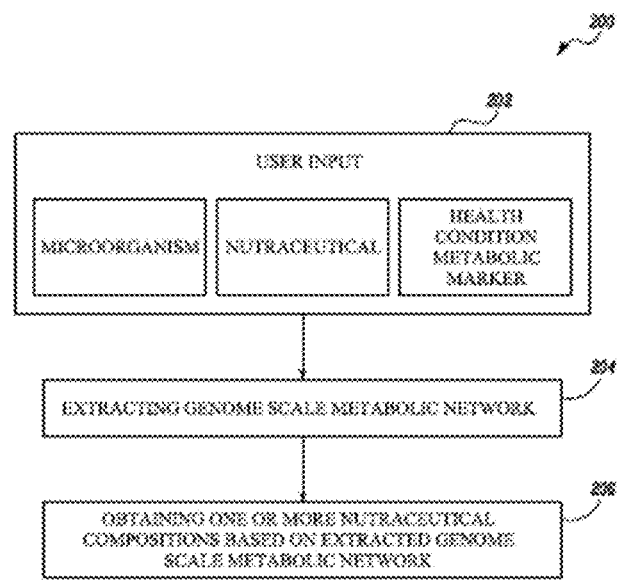
FIG. 2 illustrates an exemplary method 200 for obtaining a nutraceutical composition.

FIG. 2 illustrates an exemplary method 200 performed by the data processing system 100 of the present disclosure. At step 202 at least one user input comprising a microorganism, a nutraceutical, and a health condition is received by the control unit 108. Examples of such microorganisms, nutraceuticals and health conditions are described herein.

At step 204 a genome scale metabolic network of the microorganism is extracted from the database 108 and at step 206 a nutraceutical composition that is based on the extracted genome-scale metabolic network is generated by the control unit 108. Further, in an embodiment, a plurality of nutraceutical compositions may also be generated allowing the user to screen and select the composition with the most optimal effect on the health condition under consideration. In this specific embodiment, the composition generated is combination of the microorganism and the nutraceutical.

Figure 3:
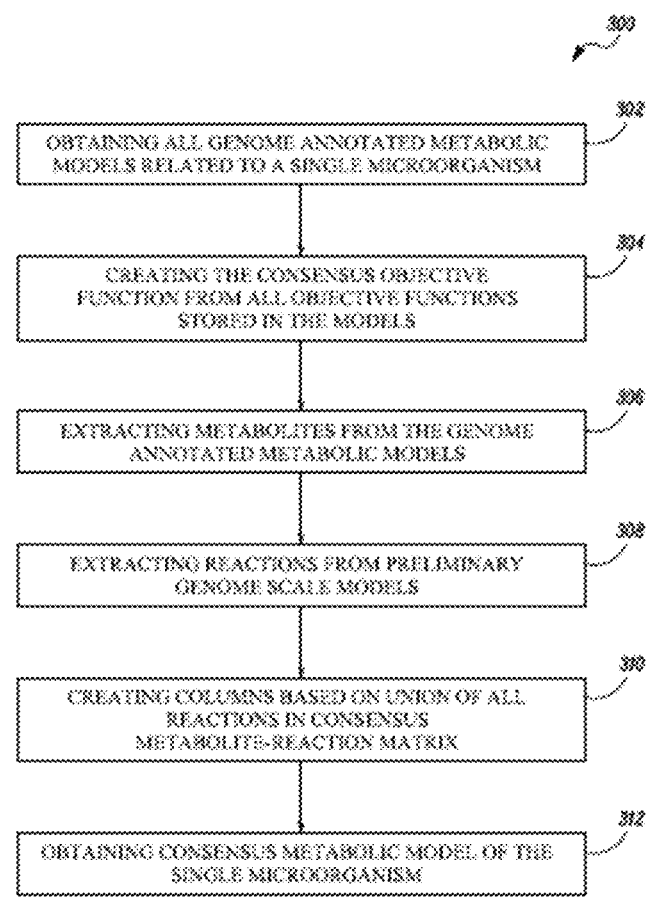
FIG. 3 illustrates the process 300 of generating the genome-scale metabolic network for a microorganism.

FIG. 3 illustrates the process 300 of generating the genome-scale metabolic network for a microorganism. At step 302 all the genome annotated metabolic models related to a single microorganism are obtained and used at step 304 to create a consensus objective function from all the objective functions stored in the models.

The objective function in the genome annotated metabolic models is a set of one or more optimization functions which aims to either maximize or minimize the flux through a set of metabolites that is either processed or internalized by the microorganism and the markers of the one or more health conditions. The maximisation function is represented through either linear or polynomial inequalities for the one or more metabolites of the microorganisms.

At step 306 the metabolites from all the genome annotated metabolic models related to the single microorganism are extracted and added to a consensus metabolite-reaction matrix, the matrix representing the combination of the information from all the metabolic models. Rows are created in the consensus metabolite-reaction matrix based on the union of all the metabolites from all the genome annotated metabolic models.

At step 308 the metabolic reactions are extracted from annotated metabolic models related to the single microorganism and at step 310 columns are created in the consensus metabolite-reaction matrix based on the union of all the metabolic reactions that are extracted.

At step 312 a consensus metabolic model of the single microorganism is obtained from the steps described above.

Figure 4:
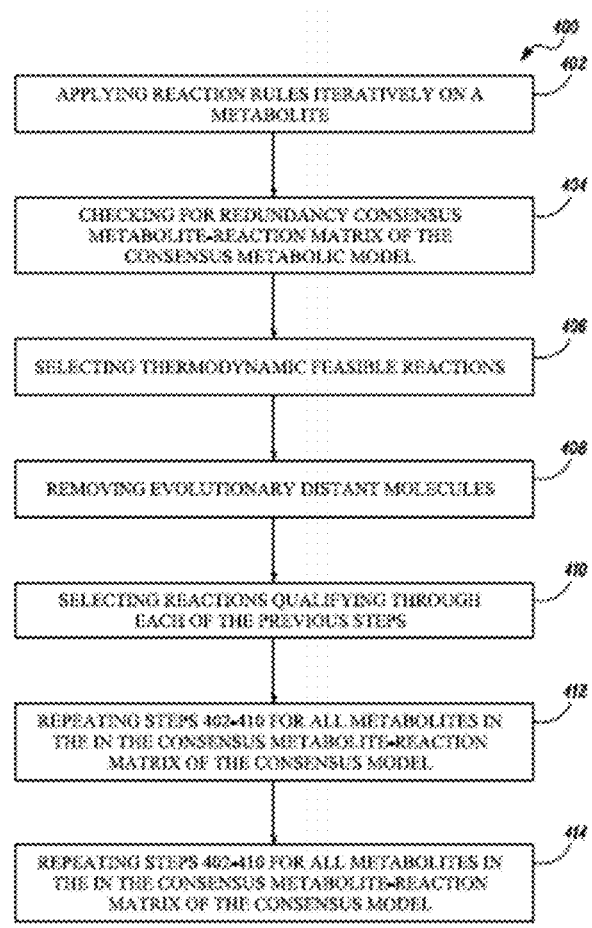
FIG. 4 illustrates the method 400 of applying one or more sets of reaction rules to the consensus metabolic model to obtain the genome-scale metabolic network for a microorganism.

FIG. 4 illustrates the method 400 of applying one or more sets of reaction rules to the consensus metabolic model to obtain the genome-scale metabolic network for a microorganism.

Once the consensus metabolic model is obtained, at step 402 one or more sets of reaction rules are applied iteratively on a specific metabolite, $m_i$. At step 404 the consensus metabolite-reaction matrix of the model is checked for redundancy of the metabolite and the reactions pertaining to it. At step 406 the thermodynamically feasible reactions pertaining to the metabolite are selected in the metabolite-reaction matrix, based on group contribution method.

The group contribution method is, briefly, a method to estimate and predict thermodynamic and other properties from molecular structures. The method is well known and may be implemented by a person skilled in the art without difficulty.

At step 408 those molecules that are evolutionary distant molecules, having a Tanimoto coefficient less than 0.7, are removed from the reactions. At step 410 only those reactions qualifying through each of the previous steps are included. At step 412 the previous steps 402-410 are repeated for all the metabolites in the consensus metabolite-reaction matrix of the consensus model. Finally, once the processing steps are performed for the metabolic reactions in the model, at step 414 the genome-scale metabolic network for the microorganism is obtained.

This genome scale metabolic network is considerably optimized from all the previous models related to the specific microorganism in the database 112 as any gaps in the information related to the metabolic networks are filled using first, the steps involved in forming the consensus metabolic model, and then through the steps of the application of the reaction rules which are able to predict reactions which may be incomplete or absent in the models.

Figure 5:
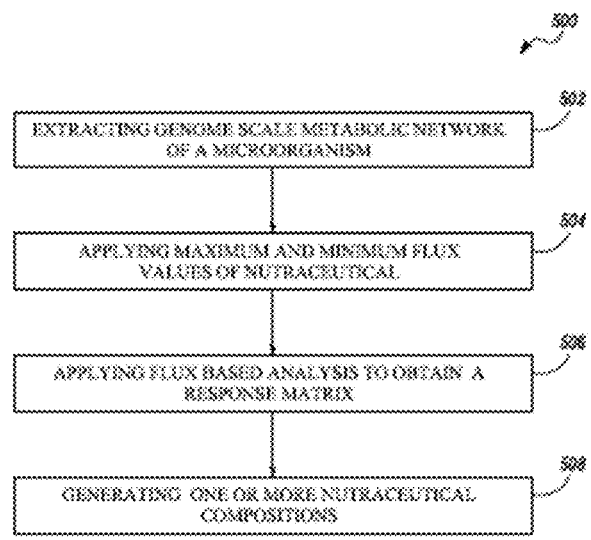
FIG. 5 illustrates the steps for the method 500 for generating the nutraceutical composition.

FIG. 5 illustrates the steps for the method 500 for generating the nutraceutical composition. Referring to step 502, the genome scale metabolic network generated through the methods 300 and 400 is extracted. As in the case of the genome annotated metabolic models, the genome-scale metabolic network is stored in the form of a metabolite-reaction matrix that comprises all the reaction constraints associated with metabolic reactions represented in the metabolite-reaction matrix.

At step 504 the maximum and minimum flux values of the nutraceutical is applied to one or more rows of the metabolite-reaction matrix of the metabolic network.

At step 506 a constraints-based application is applied to the genome-scale metabolic network and the nutraceutical to obtain a response matrix that describes the flux distribution that maximises or minimises the levels of the metabolic marker of the health condition that is specified by the user. The response matrix may be stored in the database 112.

In one aspect, a constraints-based application is the preferred methodology to obtain the flux distribution results. The most commonly used constraints-based methodologies applicable to the method described herein include, but are not limited to flux balance analysis (FBA), regulatory flux balance analysis (rFBA), flux variability analysis (FVA), minimization of metabolic adjustment (MoMA), and regulatory on-off minimization (ROOM). Most preferably, flux based analysis is used.

At step 508 the control unit 108 screens the response matrix for the optimal dosage amounts of the composition constituents (the microorganism and the nutraceutical) and reports the optimal compositions (FIG. 11) or, alternatively, the user may screen the response matrix and select the optimal composition through the I/O unit 102.

An example implementation of the method 200 is described in greater detail with the help of the following non-limiting example. It is to be appreciated that the examples are intended to be exemplary only and that numerous changes, modifications, and alterations can be employed without departing from the scope of the presently disclosed subject matter.

In a preferred implementation, the user input is the microorganism *Faecalibacterium prausnitzii*; the nutraceuticals are fructooligosaccharides (FOS) and galactooligosaccharides (GOS); and the metabolic marker of the health condition is butyrate. On receiving the user inputs, the control unit 108 obtains the genome-scale metabolic network of *F. prausnitzii* from the database 112.

The genome-scale metabolic network is obtained through the integration of a plurality of genome annotated models related to *F. prausnitzii* to obtain a consensus model of *F. prausnitzii* and the application of one or more sets of reaction rules to the consensus model. The maximum and minimum flux values (reaction constraints) of the nutraceuticals FOS and GOS is also added to the consensus metabolic model.

Figure 6:
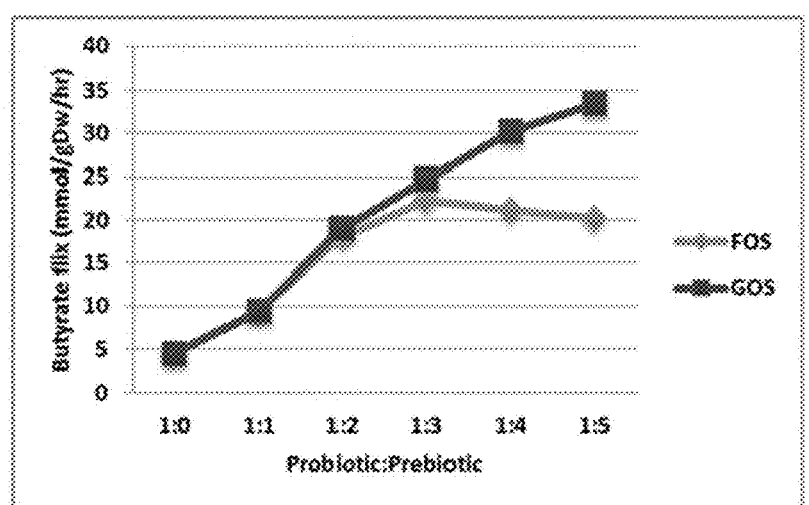
FIG. 6 demonstrates the flux distribution of butyrate in the presence at different prebiotic:probiotic ratios.
Figure 7:
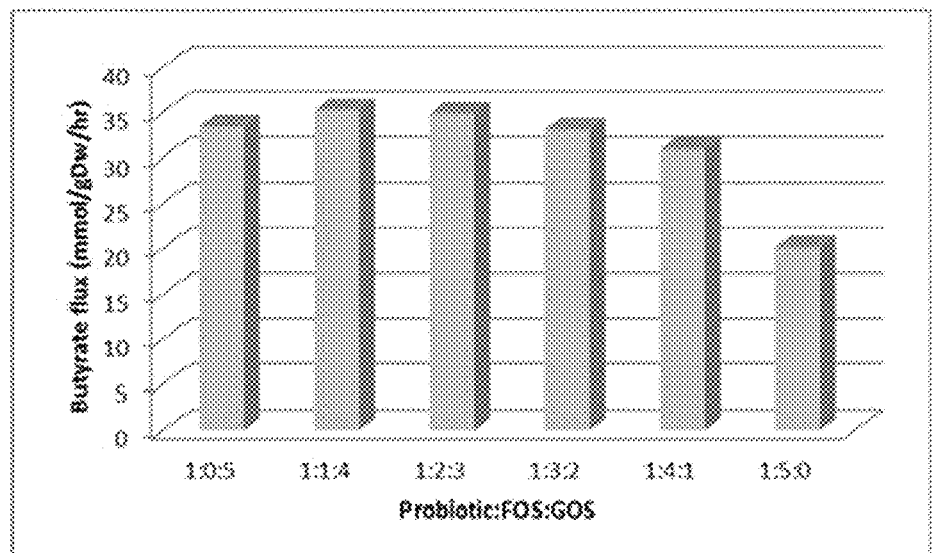
FIG. 7 demonstrates the optimal ratios of the nutraceutical composition constituents F. prausnitzii:GOS:FOS for maximum butyrate production.

Flux based analysis is then applied to the consensus metabolic model which also comprises the reaction constraints of FOS and GOS, to obtain a response matrix reflecting the flux distribution of butyrate (FIG. 6). The optimal dosage values of compositions comprising *F. prausnitzii*, FOS, and GOS are displayed on the output unit 104 (FIG. 7). The composition resulting in the optimal production of butyrate is selected by the user. In this example, the optimal composition dosage is a w/w ratio of 1:1:4 of *F. prausnitzii*:FOS:GOS (FIG. 7).

Figure 8:
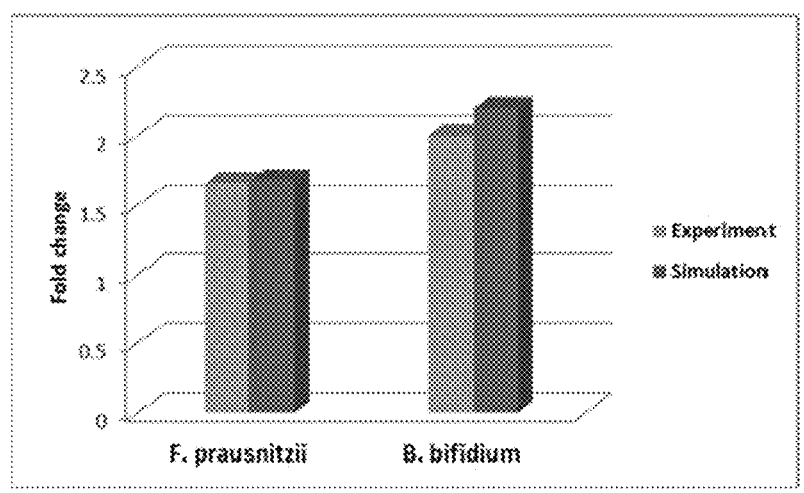
FIG. 8 and FIG. 9 depict the optimized functionality of the method described herein as compared to state-of the art models.

The accuracy of the present method in replicating in vivo conditions is demonstrated in FIG. 8. Here, the growth of the microorganisms *F. prausnitzi* and *B. bifidium* in the presence of inulin as the nutraceutical is predicted by the steps of the present method.

Figure 9:
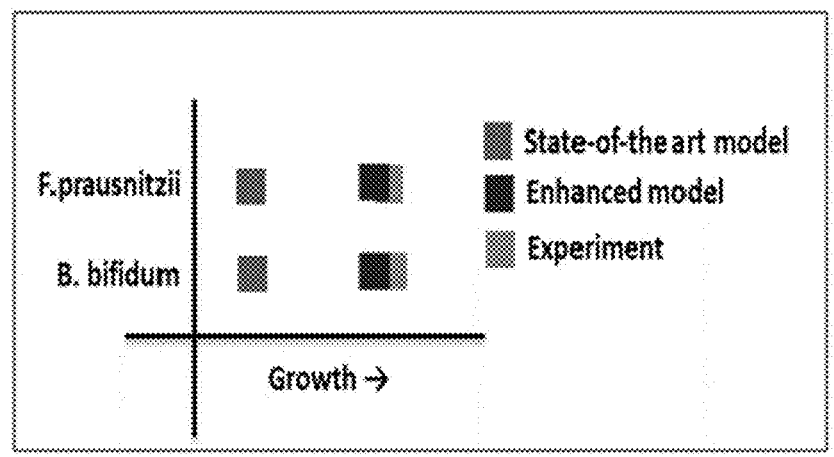

FIG. 9. also demonstrates the superiority of the present method in comparison to the state of the art models. The present method can accurately predict the results of in vivo experimental data, while the state of the art models conspicuously lack this ability. State of the art models most often lack crucial information regarding metabolic pathways and therefore have limited functional capability. The correct flux values of metabolites are most often not obtained leading to inaccuracies in the data that is generated by the state of the art models. The present method has a unique aspect of using reaction rules to optimize the genome-scale annotated models, which enable the prediction of one or more reactions which are missing from the state of the art models, thus providing very accurate estimations of the flux distributions of metabolites within the metabolic network.

In an embodiment of the present disclosure, the user input comprises a microorganism, a nutraceutical, and a plurality of metabolic markers of a health condition. Next, the genome-scale metabolic network of the microorganism is extracted by the control unit 108 from the database 112. As described previously, the metabolic network comprises a metabolite-reaction matrix which includes the reaction constraints of the metabolic reactions in the network and additionally, the reaction rules associated with the matrix are also extracted. To this, as a next step, the maximum and minimum flux values of the specific nutraceutical is added to the metabolite-reaction matrix of the genome-scale metabolic network and therefore, the metabolite-reaction matrix now comprises the reaction constraints associated with the nutraceutical. Flux-based analysis is then applied to the metabolite-reaction matrix to obtain a response matrix describing the flux distribution of the plurality of metabolic markers.

Figure 13:
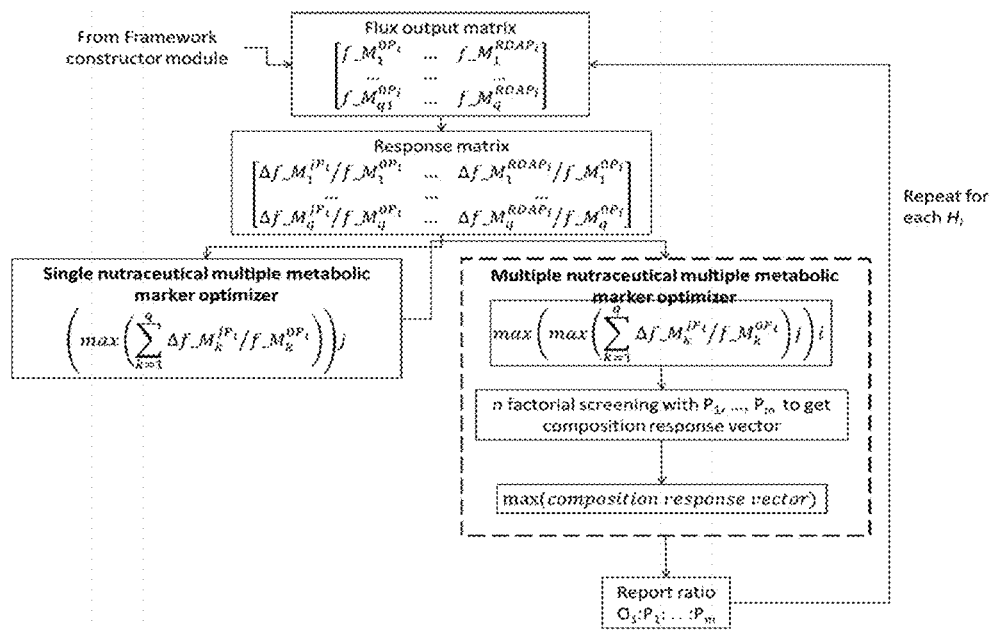
FIG. 13 demonstrates the steps for obtaining the optimal composition(s) when the user input comprises a microorganism (O), a plurality of nutraceuticals (P), and a plurality of metabolic markers for a health condition (H).

The control unit 108 screens the response matrix for the optimal dosage amount of the composition and reports the optimal compositions for the health condition (FIG. 13) or, alternatively, the user may screen the response matrix and select the optimal composition through the I/O unit 102.

In another embodiment of the present disclosure, the user input includes a microorganism, a plurality of nutraceuticals, and a plurality of metabolic markers for a health condition. Next, the genome-scale metabolic network of the microorganism is extracted by the control unit 108 from the database 112. As described previously, the metabolic network comprises a metabolite-reaction matrix which includes the reaction constraints of the metabolic reactions in the network and additionally, the reaction rules associated with the matrix are also extracted. To this, as a next step, the maximum and minimum flux values of the plurality of nutraceuticals is added to the metabolite-reaction matrix of the genome-scale metabolic network and therefore, the metabolite-reaction matrix now comprises the reaction constraints associated with the plurality of nutraceuticals. Flux-based analysis is then applied to the metabolite-reaction matrix to obtain a response matrix describing the flux distribution for the plurality of metabolic markers of the health condition.

The control unit 108 screens the response matrix optimal dosage amount of the composition for the health condition and reports the optimal compositions or, alternatively, the user may screen the response matrix and select the optimal composition through the I/O unit 102.

In a further embodiment of the present disclosure, the user input comprises a plurality of microorganisms, a plurality of nutraceuticals, and a plurality of metabolic markers of a health condition. Next, a plurality of genome-scale metabolic networks of each of the plurality of microorganisms is extracted by the control unit 108 from the database 112. As described previously, each of the metabolic network comprises a metabolite-reaction matrix which includes the reaction constraints of the metabolic reactions in each of the networks. To this, as a next step, the maximum and minimum flux values of the plurality of nutraceuticals is added to each of the metabolite-reaction matrices of the genome-scale metabolic network of each of the plurality of microorganisms. Flux-based analysis is then applied to each of the plurality metabolite-reaction matrices to obtain a plurality of response matrices describing the flux distribution for the plurality of metabolic markers of the health condition.

The control unit 108 screens the response matrix optimal dosage amount of the composition using n-factorial screening and reports the optimal compositions or, alternatively, the user may screen the response matrix and select the optimal composition through the I/O unit 102.

Figure 10:
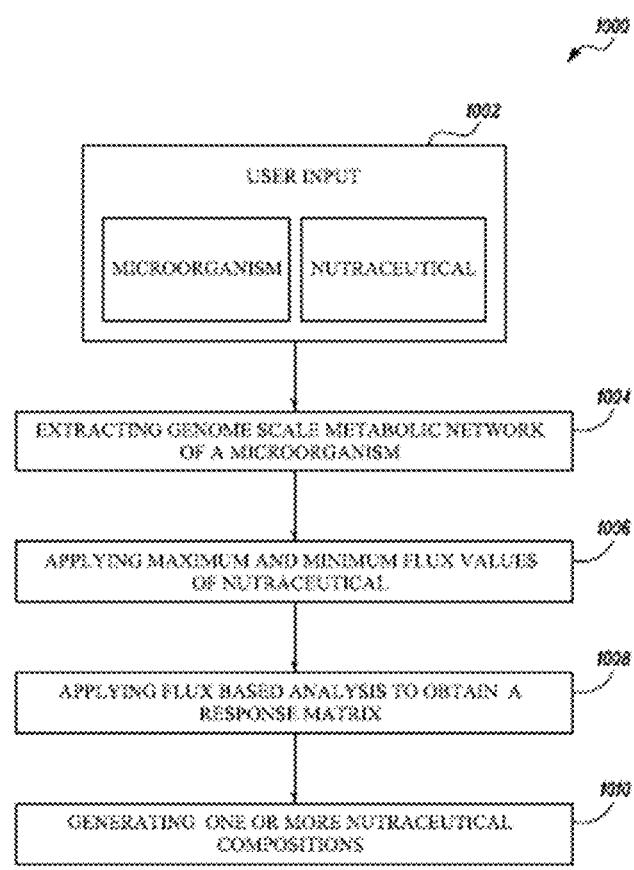
FIG. 10 illustrates a method 1000 for obtaining one or more compositions for a plurality of health conditions.

FIG. 10 illustrates a method 1000 for obtaining one or more compositions for a plurality of health conditions. Referring to step 1002, a user input is received by the control unit 108 via the I/O unit 102. The user input comprises a microorganism and a nutraceutical. At step 1004, the genome-scale metabolic network corresponding to the microorganism is extracted from the database 112.

The generation of the genome-scale metabolic network is described in methods 300 and 400. Briefly, the genome-scale metabolic network of the microorganism is obtained through the integration of a plurality of genome annotated models related to the microorganism to obtain a consensus metabolic model of the microorganism and the application of one or more sets of reaction rules to the consensus model.

At step 1006, the maximum and minimum flux values of the nutraceutical are obtained and added to the genome-scale metabolic network. As described previously, each of the metabolic network comprises a metabolite-reaction matrix which includes the reaction constraints of the metabolic reactions in each of the networks. At the addition of the flux values of the nutraceutical, the network now comprises the reaction constraints associated with the reactions of the metabolic network and the nutraceutical.

At step 1008 a constraints-based application is applied to the genome-scale metabolic network and the nutraceutical to obtain the flux distribution that maximises or minimises the levels of all the metabolic markers of the health conditions that are stored in the database 112.

In one aspect, a constraints-based application is the preferred methodology to obtain the flux distribution results. The most commonly used constraints-based methodologies applicable to the method described herein include, but are not limited to flux balance analysis (FBA), regulatory flux balance analysis (rFBA), flux variability analysis (FVA), minimization of metabolic adjustment (MoMA), and regulatory on-off minimization (ROOM). Most preferably, flux based analysis is used.

At step 1010 the flux distribution is stored in the database 112 as a response matrix. The control unit 108 reports the response matrix, through the I/O unit 102. The response matrix reports all the health conditions for which one or more of the compositions, comprising the microorganism and the nutraceutical, are beneficial to alleviate the health conditions. In an embodiment, the compositions with the optimal dosages are either generated by the control unit 108 or the user screens the matrix to identify the compositions with the optimal dosages.

Figure 11:
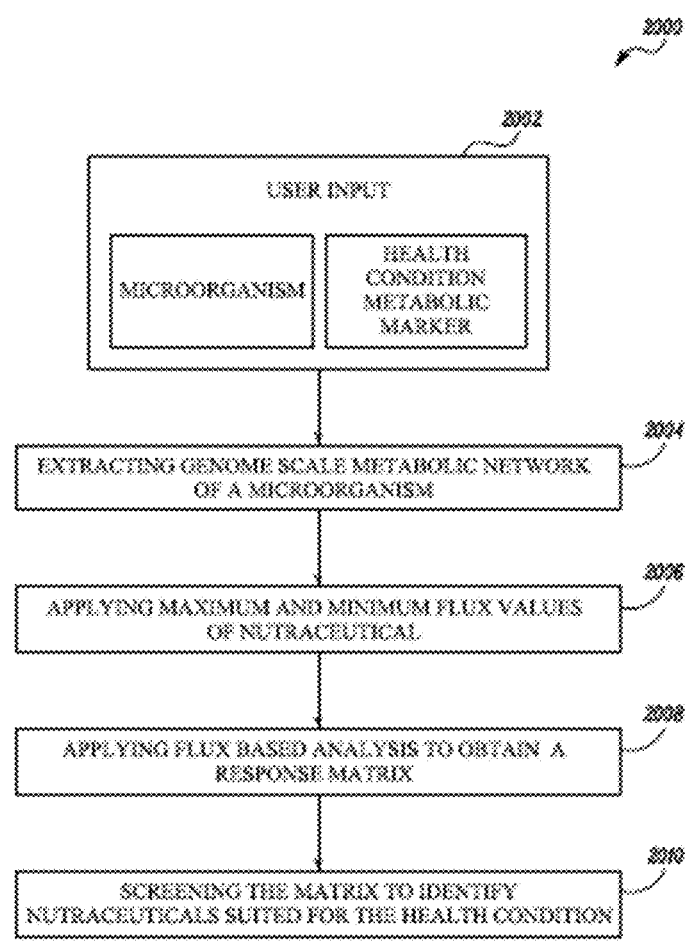
FIG. 11 illustrates a method 2000 for obtaining a plurality of nutraceutical beneficial for a health condition.
Figure 12:
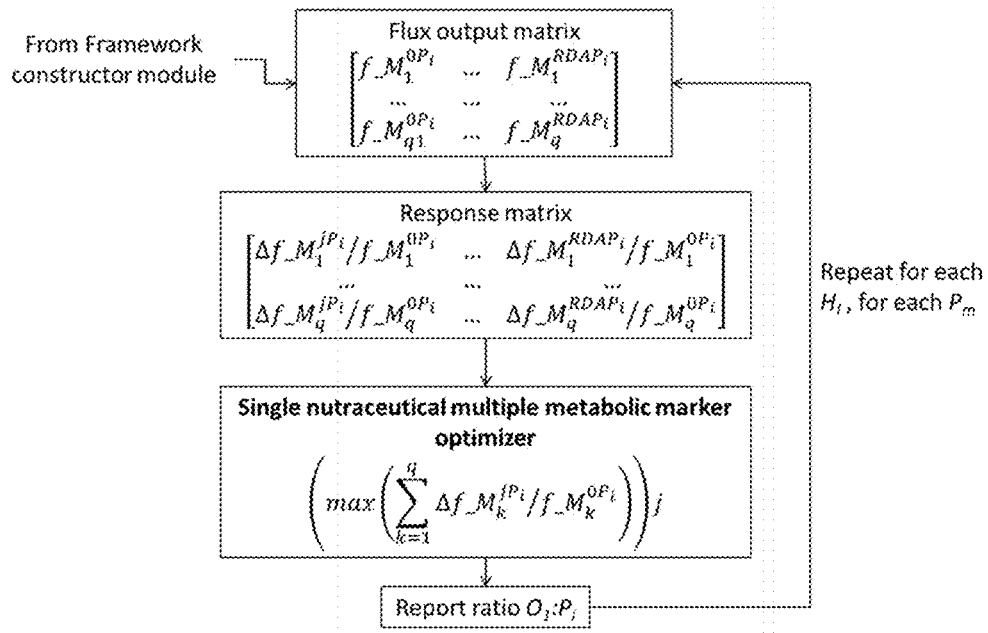
FIG. 12 demonstrates the steps for obtaining the optimal composition(s) when the user input comprises a microorganism (O), a nutraceutical (P), and a plurality of metabolic markers for a health condition (H).

FIG. 11 illustrates a method 2000 for obtaining a plurality of nutraceuticals beneficial for a health condition. Referring to step 2002, a user input is received by the control unit 108 via the I/O unit 102. The user input comprises a microorganism and a metabolic marker for a health condition. At step 2004, the genome-scale metabolic network corresponding to the microorganism is extracted from the database 112. The network is extracted along with an associated set of reaction rules.

The generation of the genome-scale metabolic network is described in methods 300 and 400. Briefly, the genome-scale metabolic network of the microorganism is obtained through the integration of a plurality of genome annotated models related to the microorganism to obtain a consensus metabolic model of the microorganism and the application of one or more sets of reaction rules to the consensus model.

At step 2006, the maximum and minimum flux values of all the nutraceutical present in the database are obtained and added to the genome-scale metabolic network. As described previously, each metabolic network comprises a metabolite-reaction matrix which includes the reaction constraints of the metabolic reactions in each of the networks. At the addition of the flux values of the plurality of nutraceuticals, the network now comprises the reaction constraints associated with the reactions of the metabolic network and the plurality of nutraceuticals.

At step 2008 a constraints-based application is applied to the genome-scale metabolic network and the nutraceutical to obtain a response matrix that describes the flux distribution that maximises or minimises the levels of all the metabolic marker of the health conditions that are stored in the database 112.

In one aspect, a constraints-based application is the preferred methodology to obtain the flux distribution results. The most commonly used constraints-based methodologies applicable to the method described herein include, but are not limited to flux balance analysis (FBA), regulatory flux balance analysis (rFBA), flux variability analysis (FVA), minimization of metabolic adjustment (MoMA), and regulatory on-off minimization (ROOM). Most preferably, flux based analysis is used.

The response matrix may be stored in the database 112. This response matrix comprises a plurality of compositions comprising the microorganism and the plurality of nutraceuticals which are beneficial for the health condition. At step 2010 the response matrix is extracted by the control unit 108 and the user screens the matrix to identify the nutraceuticals suited for the health condition.

While aspects of the present disclosure have been particularly shown, and described with reference to the embodiments above, it will be understood by those skilled in the art that various additional embodiments may be contemplated by the modification of the disclosed machines, systems, and methods without departing from the spirit and scope of what is disclosed. Such embodiments should be understood to fall within the scope of the present disclosure as determined based upon the claims and any equivalents thereof.

We claim:

1. A method for obtaining a nutraceutical composition for a health condition comprising:
   receiving, by a control unit, at least one user input including a microorganism, a nutraceutical, and the health condition;
   extracting, by the control unit, at least one genome-scale metabolic network corresponding to the user input, from a database having information related to a plurality of microorganisms, nutraceuticals, metabolic markers of a plurality of health conditions, and one or more sets of reaction rules obtained from enzymes of the plurality of microorganisms,
   wherein the at least one genome-scale metabolic network is extracted by applying the one or more sets of reaction rules to a consensus metabolic model of the microorganism,
   wherein the consensus metabolic model comprises a combination of a plurality of genome annotated metabolic models associated with the microorganism; and generating, by the control unit, from the genome-scale metabolic network, the nutraceutical composition, wherein the generating comprises:

obtaining, by the control unit, from the genome-scale metabolic network, a response matrix describing a flux distribution of at least one metabolic marker of the health condition, screening, by the control unit, the response matrix to identify the nutraceutical composition comprising a combination of the microorganism and the nutraceutical suited to the health condition, and reporting, by the control unit, the nutraceutical composition.

2. The method as claimed in claim 1, wherein the information includes:

the plurality of genome annotated metabolic models of the plurality of microorganisms;

a plurality of reaction constraints for metabolic pathways of the plurality of microorganisms; and maximum and minimum flux values of the plurality of nutraceuticals.

3. The method as claimed in claim 1, wherein generating the nutraceutical composition comprises:

extracting, by the control unit, the at least one genome-scale metabolic network corresponding to the user input;

applying, by the control unit, the maximum and minimum flux values of the nutraceutical corresponding to the user input; and applying, by the control unit, one or more of the plurality of reaction constraints for metabolic pathways of one or more of the plurality of microorganisms to obtain a response matrix.

4. The method as claimed in claim 1, wherein the microorganism is selected from group consisting of species from genera *Lactobacillus, Feacalibacterium, Bifidobacterium, Ruminococcus, Coprococcus, Dorea, Lachnospira, Roseburia, Butyrivibrio, Clostridium, Megamonas, Acidaminococcus, Succinispira, Megasphaera, Lactonifactor, Dialister, Pelosiunus, Veillonella, Acidamonas, Megamonas, Akkermansia*, and combinations thereof.

5. The method as claimed in claim 1, wherein the metabolic markers are selected from the group consisting of short chain fatty acids comprising acetate, propionate, and lactate, lipids, carbohydrates, butyrates, bile salts, siderophores, insulin, and combinations thereof.

6. The method as claimed in claim 1, wherein the health condition is selected from the group consisting of metabolic disorders comprising obesity, Cardiovascular Disease, and Type I and Type II diabetes, immunological disorders such as inflammatory bowel diseases, Crohn's disease, and irritable bowel syndrome, food allergies, asthma, acute infections, nurological disorders comprising depression, and anxiety, and combinations thereof.

7. A method for obtaining at least one nutraceutical composition for a plurality of health conditions comprising:

receiving, by a control unit, at least one user input including a microorganism, and a nutraceutical;

extracting, by the control unit, at least one genome-scale metabolic network corresponding to the user input, from a database having information related to a plurality of microorganisms, nutraceuticals and metabolic markers of a plurality of health conditions, and one or more sets of reaction rules obtained from enzymes of the plurality of microorganisms, wherein the genome-scale metabolic network is extracted by applying the one or more sets of reaction rules to a consensus metabolic model of the microorganism, wherein the consensus metabolic model comprises a combination of a plurality of genome annotated metabolic models associated with the microorganism; and generating, by the control unit, from the genome-scale metabolic network, the at least one nutraceutical composition for the plurality of health conditions, wherein the generating comprises:

obtaining, by the control unit, from the genome-scale metabolic network, a response matrix describing a flux distribution of the plurality of metabolic markers of the plurality of health conditions, screening, by the control unit, the response matrix to identify the at least one nutraceutical composition comprising a combination of the microorganism and the nutraceutical suited to the plurality of health conditions, and reporting, by the control unit, the at least one nutraceutical composition for the plurality of health conditions.

8. A method for obtaining a plurality of nutraceuticals for a health condition comprising:

receiving, by a control unit, at least one user input including a microorganism, and a health condition;

extracting, by the control unit, at least one genome-scale metabolic network corresponding to the user input, from a database having information related to a plurality of microorganisms, nutraceuticals and metabolic markers of a plurality of health conditions, and one or more sets of reaction rules obtained from enzymes of the plurality of microorganisms, wherein the genome-scale metabolic network is extracted by applying the one or more sets of reaction rules to a consensus metabolic model of the microorganism, wherein the consensus metabolic model comprises the combination of a plurality of genome annotated metabolic models associated with the microorganism; and generating, by the control unit, from the genome-scale metabolic network and the health condition of the user input, the plurality of nutraceuticals suited for the health condition, wherein the generating comprises:

obtaining, by the control unit, from the genome-scale metabolic network, a response matrix describing the flux distribution of at least one metabolic marker of the health condition and the flux distribution of the plurality of nutraceuticals, and reporting, by the control unit, the response matrix.

9. A system for obtaining a nutraceutical composition comprising:

a display unit;

at least one database having information related to a plurality of microorganisms, nutraceuticals and metabolic markers for a plurality of health conditions, and one or more sets of reaction rules derived from the enzymes reported within the plurality of microorganisms;

a control unit operatively coupled to the display unit, and the at least one database, the control unit being configured to:

receive at least one user input via the display unit, the user input being selected from the group consisting of a microorganism, a nutraceutical, a health condition and combinations thereof;
 extract, from the database, at least one genome-scale metabolic network based on the user input,
 wherein the at least one genome-scale network is extracted by applying the one or more sets of reaction rules to a consensus metabolic model of the microorganism,
 wherein the consensus metabolic model comprises a combination of a plurality of genome annotated metabolic models associated with the microorganism; and
generate at least one nutraceutical composition based on the received at least one user input and the extracted at least one genome-scale metabolic network, wherein the generating comprises:
 obtaining, by the control unit, from the genome-scale metabolic network, a response matrix describing a flux distribution of at least one metabolic marker of the health condition,
 screening, by the control unit, the response matrix to identify the nutraceutical composition comprising a combination of the microorganism and the nutraceutical suited to the health condition, and
 reporting, by the control unit, the nutraceutical composition.

10. The method as claimed in claim 7, wherein the plurality of health conditions is selected from the group consisting of metabolic disorders comprising obesity, cardiovascular disease, and Type I and Type II diabetes, immunological disorders such as inflammatory bowel diseases, Crohn's disease, and irritable bowel syndrome, food allergies, asthma, acute infections, neurological disorders comprising depression, and anxiety, and combinations thereof.

11. The method as claimed in claim 7, wherein the microorganism is selected from group consisting of species from genera *Lactobacillus, Feacalibacterium, Bifidobacterium, Ruminococcus, Coprococcus, Dorea, Lachnospira, Roseburia, Butyrivibrio, Clostridium, Megamonas, Acidaminococcus, Succinispira, Megasphaera, Lactonifactor, Dialister, Pelosiunus, Veillonella, Acidamonas, Megamonas, Akkermansia*, and combinations thereof.

12. The method as claimed in claim 7, wherein the metabolic markers are selected from the group consisting of short chain fatty acids comprising acetate, propionate, and lactate, lipids, carbohydrates, butyrates, bile salts, siderophores, insulin, and combinations thereof.

13. The method as claimed in claim 8, wherein the microorganism is selected from the group consisting of species from genera *Lactobacillus, Feacalibacterium, Bifidobacterium, Ruminococcus, Coprococcus, Dorea, Lachnospira, Roseburia, Butyrivibrio, Clostridium, Megamonas, Acidaminococcus, Succinispira, Megasphaera, Lactonifactor, Dialister, Pelosiunus, Veillonella, Acidamonas, Megamonas, Akkermansia*, and combinations thereof.

14. The method as claimed in claim 8, wherein the health condition is selected from the group consisting of metabolic disorders comprising obesity, cardiovascular disease, and Type I and Type II diabetes, immunological disorders such as inflammatory bowel diseases, Crohn' s disease, and irritable bowel syndrome, food allergies, asthma, acute infections, neurological disorders comprising depression, and anxiety, and combinations thereof.

15. The method as claimed in claim 8, wherein the metabolic markers are selected from the group consisting of short chain fatty acids comprising acetate, propionate, and lactate, lipids, carbohydrates, butyrates, bile salts, siderophores, insulin, and combinations thereof.

\* \* \* \* \*